United States Patent [19]

Hermann et al.

[11] Patent Number: 4,759,768
[45] Date of Patent: Jul. 26, 1988

[54] JOINT PROSTHESIS, IN PARTICULAR FINGER JOINT PROSTHESIS

[76] Inventors: Thierry Hermann, Wenkenhaldenweg, 15, 4125 Richen, Switzerland; Michel Pequignot, 16 Villa Désiré Filleaud, 92140 Clamart, France

[21] Appl. No.: 15,107

[22] Filed: Feb. 13, 1987

[51] Int. Cl.⁴ .............................. A61F 2/42; A61F 2/30
[52] U.S. Cl. ........................................... 623/21; 623/18
[58] Field of Search ..................... 623/18-21, 623/16

[56] References Cited

U.S. PATENT DOCUMENTS

| | | | |
|---|---|---|---|
| 3,772,709 | 11/1973 | Swanson | 623/18 X |
| 4,011,603 | 3/1977 | Steffee | 623/21 |
| 4,059,854 | 11/1977 | Laure | 623/21 |
| 4,150,444 | 4/1979 | Hagert | 623/21 |
| 4,304,011 | 12/1981 | Whelan, III | 623/21 |
| 4,352,212 | 10/1982 | Greene et al. | 623/21 |

FOREIGN PATENT DOCUMENTS

| | | | |
|---|---|---|---|
| 1484143 | 5/1967 | France | 623/21 |
| 2321871 | 3/1977 | France | 623/21 |
| 2356406 | 1/1978 | France | 623/18 |

Primary Examiner—Ronald L. Frinks
Attorney, Agent, or Firm—Charles E. Brown; Charles A. Brown

[57] ABSTRACT

A joint prosthesis comprises two pins each designed to be directly or indirectly inserted into a respective one of the two bones to be joined. Operative between the pins are articulation surfaces comprising, in the case of one of the pins, referred to as the carrier pin, two domes centered on an axis perpendicular to the carrier pin, oriented in opposite directions relative to each other and carried by the carrier pin. In the case of the other pin, referred to as the carried pin, the articulation surfaces comprises two further domes each complementary to a respective one of the first-mentioned domes, and thus adapted to be engaged therewith, carried by the carried pin. The domes of the carrier pin are carried by respective pegs which are movable transversely relative to the two pins, the carrier pin comprising two arms each having two respective aligned housings in which the pegs are slidably inserted.

17 Claims, 2 Drawing Sheets

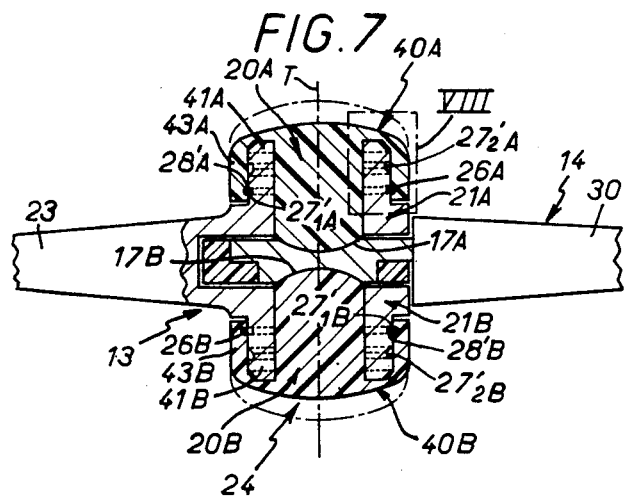
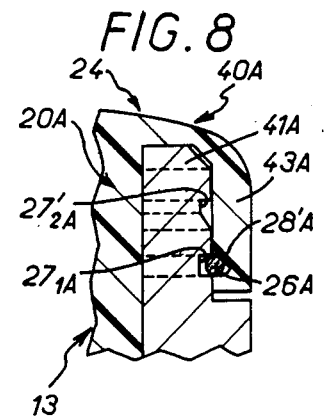
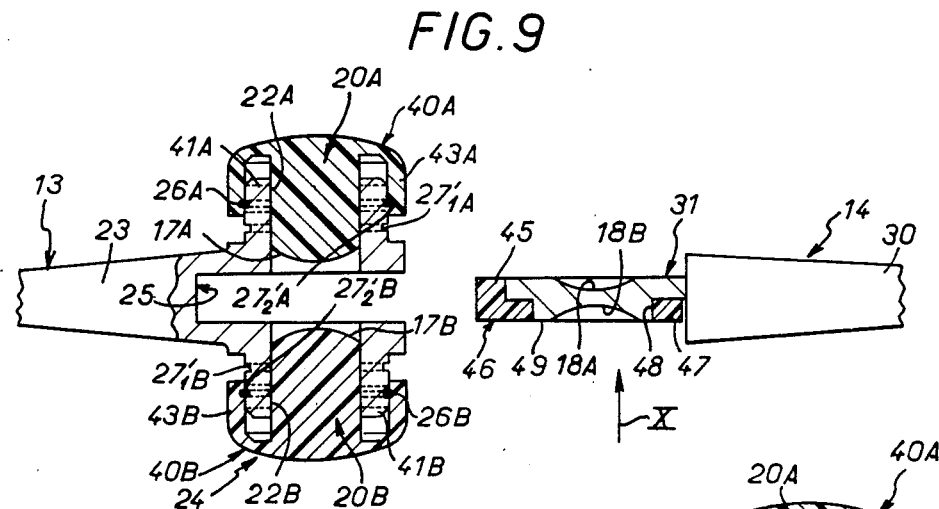
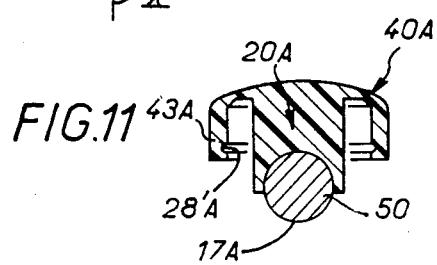
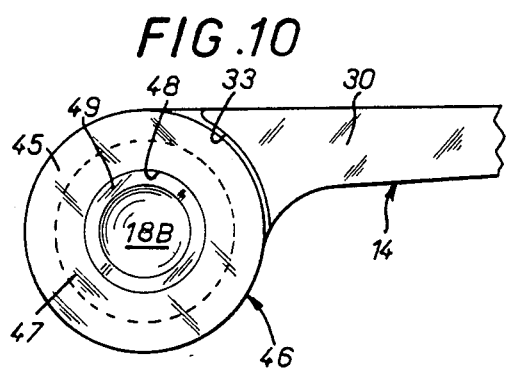
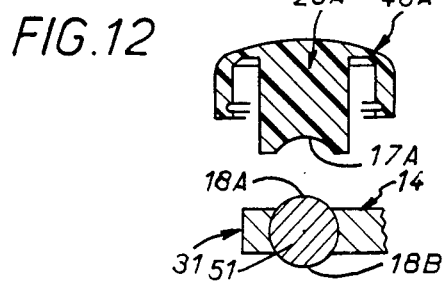

JOINT PROSTHESIS, IN PARTICULAR FINGER JOINT PROSTHESIS

The present invention is generally concerned with joint prostheses, and is more particularly directed to those enabling pivoting about one axis only.

This is the case, for example, with the joints between the successive phalangeal bones of a finger which, as is known, constitute trochlear diarthroses, that is to say joints in which one bone rolls on another by means of a groove that the latter features for this purpose and which forms a pulley.

The prostheses currently available to replace such joints in the event of traumatisms are not totally satisfactory.

Firstly there are prostheses made from flexible material, natural or synthetic rubber, for example, the mechanical strength of which is sometimes insufficient.

Then there are mechanical prostheses comprising, for example, two pins each designed to be inserted in a respective one of the two bones to be joined and, operative between said pins, a simple yoke attached to one of them and a pivot pin attached to the other.

Mechanical prostheses of this kind have two disadvantages.

Firstly, they do not lend themselves, without breakage or unacceptable structural complications, to any possibility of dislocation, or in other words of disengagement, even where this possibility is desirable from a physiological point of view.

Also, as the articulation surfaces that they employ are open surfaces, that is to say surfaces open laterally at a number of locations, being successive cylindrical surfaces, they may gradually seize up as a result of invasion by bone tissue.

However, prostheses have also been proposed in which the articulation surfaces are advantageously internal surfaces which, as they are not open laterally to the outside, are therefore protected in the necessary way.

This is the case, for example, in French Patent No. 1,484,143 and in U.S. Pat. No. 4,059,854.

In practise in the corresponding joint prostheses which, as previously, are prostheses equipped with pins for fitting them, the articulation surfaces comprise, for one of the pins, referred to hereinafter for convenience as the carrier pin, two more or less spherical or spheroidal domes which, both centered on an axis perpendicular to said carrier pin and oriented away from each other, are carried by said carrier pin, whereas, for the other of said pins, referred to hereinafter for convenience as the carried pin, they comprise two other more or less spherical or spheroidal domes respectively complementary to the previously mentioned domes and thus adapted to be engaged with them, carried by said carried pin.

However, because the resulting articulation surfaces are internal surfaces, it is necessary in both cases to force-fit one of the pins relative to the other when the prosthesis is implanted.

Apart from the fact that such force fitting is not necessarily easily implemented, it inevitably requires that the part concerned of at least one of the pins, that forming a female member relative to the other, has some capacity for deformation, which is possibly detrimental to the subsequent strength of the assembly.

In the French patent filed under the No. 77,19625 and published under the No. 2,356,406 there is also proposed a joint prosthesis one component of which has more or less spherical or spheroidal domed articulation surfaces.

However, the articulation surfaces of the other component are outwardly oriented, entailing the risk of subsequent invasion by bone tissue, and for the purpose of engaging with the articulation surfaces of the first component they feature grooves which further accentuate this risk.

Also, this French Patent No. 77,19625 is concerned with a prosthesis the component parts of which have no pins, being fitted to the bones to be joined by means of screws; moreover, the construction of this prosthesis is relatively complex, and therefore expensive, and there seems room for doubt as to its possibility for dislocation.

A general object of the present invention is an arrangement whereby these disadvantages can be obviated.

To be more precise, its object is a joint prosthesis of the kind comprising two pins each designed to be directly or indirectly inserted into a respective one of the two bones to be joined and, operative between said pins, articulation surfaces comprising, in the case of one of the pins, herein referred to for convenience as the carrier pin, two domes centered on an axis perpendicular to said carrier pin, oriented in opposite directions relative to each other and carried by said carrier pin and, for the other of said pins, herein referred to for convenience as the carried pin, two further domes each complementary to a respective one of the first-mentioned domes and thus adapted to be engaged therewith, carried by said carried pin, this joint prosthesis being generally characterized in that the domes of the carrier pin are carried by respective pegs which are movable transversely relative to the two pins, said carrier pin comprising two arms each having two respective aligned housings in which said pegs are slidably inserted.

By virtue of their mobility the pegs employed in accordance with the invention may be moved from a relatively spaced apart standby position, in which they do not interfere with the path of movement of the carried pin at the time of its engagement relative to the carrier pin, to a relatively close together operative position in which, once the aforementioned engagement has been effected, the domes that they carry are engaged with the domes of the carried pin.

Thus the relative engagement of the carried pin with the carrier pin advantageously entails no elastic deformation of any of the essential components of either pin, which favours subsequent maintenance of a proper orientation of the pins relative to each other.

Also, by virtue of the arrangement in accordance with the invention the articulation surfaces operative between the pins are advantageously inside surfaces none of which opens directly to the outside, so that the risk of them being subject of any invasion by bone tissue is advantageously minimized.

In practise the housings in which the pegs employed to this end in accordance with the invention are movably mounted are preferably open to the outside, so that, in order to move them from their standby retracted position to their close together operative position, it is a very simple matter to operate on the pegs from the outside.

The use of the joint prosthesis in accordance with the invention is thereby greatly simplified: the relative engagement of the carried pin with the carrier pin having been effected with the pegs in the standby retracted position, all that is needed is to move them to the close together operative position, which can be done with one hand.

Also, because of the ability to move the pegs which carry them, the domes on the carrier pin can move, if required, relative to the domes on the carried pin with which they are engaged, so that a possibility of dislocation can be provided, where required, in a very simple and secure way, without risk of breakage.

However, in accordance with one embodiment of the invention there is conjointly associated with at least one of the pins, and preferably with each of them, a socket in which a tail of the pin is inserted and relative to which it can move longitudinally.

It is then the socket which is embedded, anchored or screwed into the corresponding bone cavity.

The clearance between a socket of this kind and the corresponding pin advantageously favors the possibility of dislocation at this level, conjointly with or instead of the previously mentioned possibility for this.

The characteristics and advantages of the invention will emerge from the following description given by way of example with reference to the appended diagramatic drawings in which:

FIGS. 7 and 8 are views respectively analogous to those of FIGS. 2 and 3, showing an alternative embodiment of the joint prosthesis in accordance with the invention;

FIG. 9 is a view of this alternative embodiment analogous to that of FIG. 6A;

FIG. 10 is a side view of one of the pins that this embodiment comprises, as seen in the direction of the arrow X in FIG. 9;

FIG. 11 is a view in axial cross-section repeating that of FIG. 7 in part and referring to an alternative embodiment of one of the component parts of the joint prosthesis in accordance with the invention;

FIG. 12 is a view in axial cross-section also repeating that of FIG. 7 in part and relating to another embodiment of the joint prosthesis in accordance with the invention;

Figure 1:
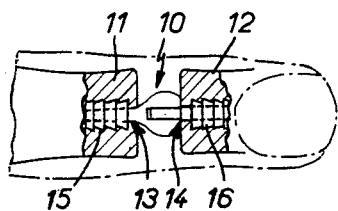
FIG. 1 is a view in axial cross-section of a joint prosthesis in accordance with the invention fitted between two phalangeal bones of a finger.

As shown in FIG. 1, the joint prosthesis 10 in accordance with the invention is designed to couple two bones 11, 12, in this instance two phalangeal bones of a finger.

To this end it comprises two pins 13, 14 which, either directly or indirectly through the intermediary as shown here and as will be described in more detail later of sockets 15, 16, are designed to be respectively inserted in the bones 11, 12 to be joined and between which are operative articulation surfaces comprising, in the case of one of them, the pin 13, referred to herein for convenience as the carrier pin, two generally spherical or spheroidal domes 17A, 17B which are carried by said carrier pin 13 and oriented in opposite directions relative to each other, and, in the case of the other, the pin 14, referred to herein for convenience as the carried pin, two other domes 18A, 18B respectively complementary to the aforementioned domes and therefore adapted to be engaged with them, carried by said carrier pin 13 and cooperating, as will be described in more detail later, with means referred to herein for convenience as restriction means adapted to enable only relative pivoting about a transverse axis T of the domes 18A, 18B of the carried pin 14 relative to the domes 17A, 17B of the carrier pin 13.

Figure 2:
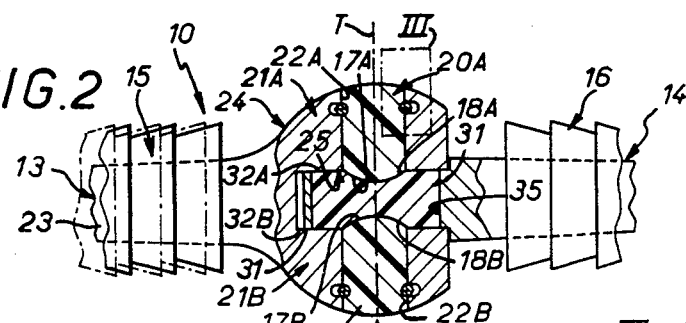
FIG. 2 is a view to a larger scale and in axial cross-section of the joint prosthesis shown in isolation.
Figure 4:
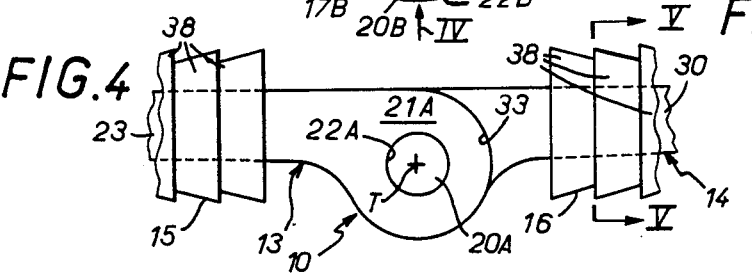
FIG. 4 is a side view of the joint prosthesis as seen in the direction of the arrow IV in FIG. 2.
Figure 5:
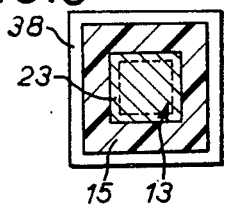
FIG. 5 is a view of it in transverse cross-section on the line V—V in FIG. 4.

The transverse axis T is substantially perpendicular to the pins 13, 14 and therefore substantially perpendicular to the bones 11, 12 concerned and is shown in chain-dotted line in FIGS. 2 and 7; its location is also schematically shown in FIG. 4.

In practise the domes 17A, 17B on the one hand and 18A, 18B on the other hand are spherical domes all centered on the transverse axis T.

As shown, each subtends a solid angle which is less than 90°, for example.

It is obvious, however, that as an alternative to this the solid angle could be greater than 90°.

In the embodiments shown in FIGS. 1 through 11 the domes 17A, 17B of the carrier pin 13 are convex and, correspondingly, the domes 18A, 18B of the carried pin are concave.

As an alternative to this, however, and as is the case with the embodiment shown in FIG. 12, which will be described in more detail later, the converse arrangement may be adopted.

Be this as it may, in accordance with the invention the domes 17A, 17B of the carrier pin 13 are carried by respective pegs 20A, 20B which are transversely mobile relative to the pins 13, 14, in practise along the transverse axis T; said carrier pin 13 comprises to this end two arms 21A, 21B each having two respective housings 22A, 22B aligned with each other along said transverse axis T in which are slidably inserted said pegs 20A, 20B.

In practise the housings 22A, 22B which are cylindrical housings with circular transverse cross-sections, are open to the outside, on the facing surfaces of the arms 21A, 21B, so that it is possible to operate on the corresponding pegs 20A, 20B from the outside.

In the embodiments specifically shown in FIGS. 1 through 6 the carrier pin 13 is solid and is made from metal, for example.

It comprises, in one piece with it, a metal tail 23 through which it is adapted to be inserted into the bone concerned, in practise through the intermediary of the socket 15, and which in the embodiment shown has a pyramid-shaped external contour with a four-sided transverse cross-section and a head 24 which, formed by the arms 21A, 21B, has a generally spheroidal outside contour but with the edge of the arms 21A, 21B terminated by a cylindrical surface of circular contour centered on the transverse axis T.

The arms 21A, 21B of the carrier pin 13 delimit between them a slot 25 perpendicular to the transverse axis T the facing surfaces of which are parallel to each other and into which the corresponding housings 22A, 22B open.

In the embodiment shown in FIGS. 1 through 6 the pegs 20A are 20B are solid and they may be synthetic material pegs, for example, chosen for biological compatibility with bone tissue.

At their inside end they form the corresponding domes 17A, 17B.

Their outside end is generally rounded off so as to merge in the operative position with the outside surface of the arms 21A, 21B, continuously therewith.

As shown, snap-fit means are preferably provided between the pegs 20A, 20B and the arms 21A, 21B which carry them adapted for locking the pegs 20A, 20B in position in their respective housing 22A, 22B.

Figure 3:
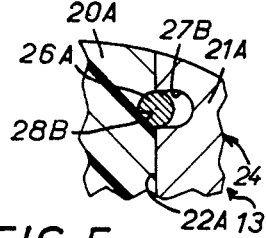
FIG. 3 shows to a larger scale the detail marked III on FIG. 2.

For example, as shown here there is provided for each of the pegs 20A, 20B an elastically deformable ring 26A, 26B, for example a ring with a localized radial slot which, disposed in a groove 27A, 27B in the arm 21A, 21B concerned adapted to contain it completely (FIGS. 6A, 6B) is adapted to cooperate conjointly with a groove 28A, 28B in the peg 20A, 20B which can accommodate it only partially (FIGS. 2, 3).

Like the carrier pin 13, the carried pin 14 comprises in one piece with it a tail 30 which has a generally pyramid-shaped outside contour with a four-sided transverse cross-section and a head reduced to a simple flange 31.

The corresponding domes 18A, 18B are respectively recessed into the plane lateral surfaces 32A, 32B of the flange 31, which are parallel to each other and substantially perpendicular to the transverse axis T.

In practise in the embodiment shown the lateral surfaces 32A, 32B of the flange 31 are slightly set back relative to the corresponding surfaces of the associated tail 30 and the shoulders 33 that the carrier pin 14 thereby features at the root of the flange 31 have, as seen in plan view, a circular contour complementary to that of the edge of the arms 21A, 21B of the carrier pin 13.

Be this as it may, the thickness of the flange 31 of the carried pin 14 is substantially equal to the width of the slot 25 in the carrier pin 13, being in practise slightly less than the latter, so that the flange 31 can be inserted into the slot 25.

In plan view, the flange 31 of the carried pin 14 has a circular outside contour, comparable with that of the head 24 of the carrier pin 13, in order to merge with the latter.

In the embodiment shown, there is a large aperture 35 in the flange 31 which therefore forms a ring into which is chased a part 36 forming the corresponding domes 18A, 18B.

In this embodiment the part 36 is in practise a plate the surfaces of which are level with the respective surfaces of the flange 31 to which it is fitted and have recessed into them, back-to-back, the domes 18A, 18B.

As previously, this plate is preferably made from a synthetic material biologically compatible with bone tissue.

Finally, in the embodiment shown and as already mentioned above, there are associated with the pins 13, 14, to be more precise with their tails 23, 30, sockets 15, 16 into which said tails 23, 30 of said pins 13, 14 are inserted and relative to which they can move longitudinally.

As also previously mentioned, the tails 23, 30 of the pins 13, 14 have a pyramid-shaped outside contour, being very slightly tapered towards their free end.

As a corollary to this, the sockets 15, 16 have a pyramid-shaped internal contour complementary to that previously mentioned.

Thus in this case the corresponding sleeve joints are pyramid-shaped.

Although the corresponding transverse cross-sections are four-sided in the embodiment shown, these transverse cross-sections could equally well be triangular.

Generally speaking, they are preferably polygonal in order to prevent under normal circumstances any rotation of the pins 13, 14 relative to their sockets 15, 16.

In the embodiment shown the sockets 15, 16 employed also have a pyramid-shaped outside contour, comparable with their inside contour.

Also, over part at least of their length they feature transverse notches 38.

The sockets 15, 16 are thus adapted be force-fitted into the bones 11, 12 to be joined, after appropriately excavating the latter and squaring off the end concerned.

They are then anchored into the bones 11, 12 by these notches 38.

Be this as it may, once the sockets 15, 16 have been fitted into the bones 11, 12 to be joined, the tails 23, 30 of the pins 13, 14 are inserted into the sockets 15, 16.

Figure 6A:
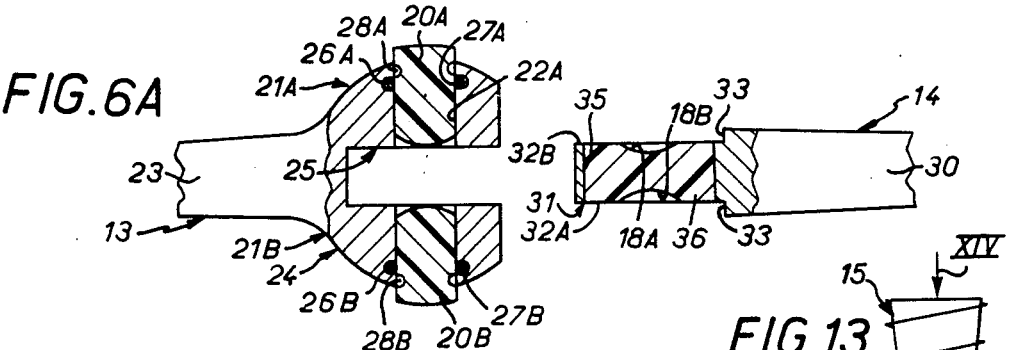
FIGS. 6A, 6B are views in axial cross-section analogous to that of FIG. 2 which illustrate two successive phases of implanting the joint prosthesis in accordance with the invention.
Figure 6B:
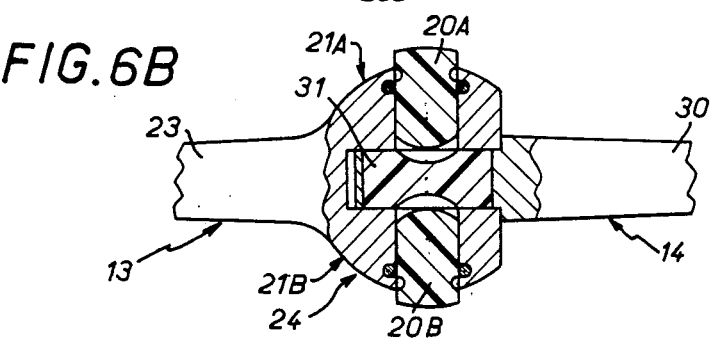

The pegs 22A, 22B of the carrier pin 13 being in the position in which they project relative to the arms 21A, 21B of the latter, and thus moved apart from each other, with the corresponding elastically deformable rings 26A, 26B elastically retracted into the grooves 27A, 27B in the arms 21A, 21B (FIG. 6A), the flange 31 of the carried pin 14 is then inserted in the thus exposed slot 25 on the carried pin 13, until its circular shoulders 33 come into contact with the corresponding edge of said arms 21A, 21B (FIG. 6B).

The domes 18A, 18B of the flange 31 of the carried pin 14 are then aligned with the pegs 20A, 20B of the carrier pin 13.

It is then sufficient to push the pegs 20A, 20B down into their housings 22A, 22B, or in other words to move them towards each other, until the domes 17A, 17B forming their inside ends become engaged with the corresponding domes 18A, 18B of the flange 31 of the carried pin 14.

At the end of this operation the outside ends of the pegs 20A, 20B are advantageously continuous with the corresponding rounded surfaces of the arms 21A, 21B to which they are fitted and the elastically deformable rings 26A, 26B conjointly expand elastically into the grooves 28A, 28B in the pegs 20A, 20B, which advantageously produces an audible "click" indicating that the assembly has been executed correctly.

The tendons concerned are then sutured in the usual way.

It will be understood that because the domes 18A, 18B of the carried pin 14 form part of respective separate surfaces the only movement for which there is any natural provision between the carried pin 14 and the carried pin 13 is a movement of rotation about the transverse axis T on which the domes 18A, 18B are both centered.

The "restriction" means mentioned above are thus obtained in a very simple way.

In the embodiment shown this restriction effect is confirmed by the fact that the carried pin 14 is conjointly engaged by a flange 31 in the carrier pin 13, but with a greater or lesser degree of assembly clearance, however.

In FIGS. 1 and 6B relating to this embodiment it has been assumed that there is no assembly clearance.

Clearance has been shown in FIG. 7, however, which relates to an embodiment to be described later.

Be this as it may, when the pegs 20A, 20B employed in accordance with the invention have their domes 17A, 17B engaged in the domes 18A, 18B of the carried pin 14, in the manner described, they normally hold the latter in engagement with the carrier pin 13.

As will be readily understood, however, the joint prosthesis in accordance with the invention provides the possibility of dislocation in a very simple and secure way and without risk of breakage.

If any dislocation occurs, it is preferably operative between at least one of the pins 13, 14 and the corresponding sockets 15, 16, by virtue of longitudinal movement of the pin 13, 14 relative to the socket 15, 16.

Because, as state above, the sleeve joint between the tail 23, 30 of the pin 13, 14 and its socket 15, 16 is advantagously pyramid-shaped, there is no possibility of rotation between it and the socket under normal circumstances.

On the other hand, should dislocation occur the possibility of rotation is advantageously developed, clearance then arising between the tail 23, 30 of the pin 13, 14 concerned and its socket 15, 16 because of its longitudinal displacement relative to the latter.

This possibility of rotation, which remains limited, can advantageously make it possible for the relative torsional force applied to the bones concerned not to result in unwanted detachment of the prosthesis.

The bones concerned are then drawn back together in the natural way by the tendons normally operative between them.

It is to be understood that the sockets 15, 16 are preferably made from a synthetic material biologically compatible with bone tissue.

The notches 38 that they comprise, and which are operative in the manner of barbs, may be sufficient for implanting them in the corresponding bone cavities.

As the material of the latter is in practise a spongy material exhibiting fast growth, the gaps between the notches 38 are very soon affected by considerable invasion of bone tissue, consolidating their attachment to the bones concerned.

As an alternative to this, however, the sockets 15, 16 may be embedded in cement.

In the embodiment shown in FIGS. 7 through 10 the pegs 20A, 20B of the carrier pin 13 are fixed to respective caps 40A, 40B through which they cover at least in part the arms 21A, 21B of the carrier pin 13.

In practise each of the arms 21A, 21B then forms an annular boss 41A, 41B in which is the corresponding housing 22A, 22B and which therefore has a well configuration, and the associated cap 40A, 40B comprises a skirt 43A, 43B through which it surrounds the annular boss 41A, 41B over at least part of its height.

A cap 40A, 40B of this kind has various advantages.

Firstly, as schematically represented in chain-dotted line in FIG. 7, it may have different thicknesses along the transverse axis T.

Thus for the same joint prosthesis, that is to say for a joint prosthesis consisting of the same pins 13, 14, it is possible to provide different caps 40A, 40B and to choose from these ones with the thickness best adapted to the thickness of the finger to be treated.

The use of a cap 40A, 40B also and advantageously makes it possible to extend over a greater diameter the snap-fit means provided for locking the pegs 20A, 20B in position.

In the embodiment shown in FIGS. 7 through 10 these snap-fit means are no longer operative directly between the pegs 20A, 20B and their housings 22A, 22B but between the skirt 43A, 43B of the cap 40A, 40B to which they are fastened and the annular boss 41A, 41B of the corresponding arm 21A, 21B.

Because these snap-fit means thus extend over a diameter greater than that of the pegs 20A, 20B alone, their manufacture is facilitated and their operation enhanced.

In the embodiment shown in FIGS. 7 through 10 the snap-fit means, which comprise an elastically deformable ring 26A, 26B, as previously, are in practise operative at two different levels.

Although there is provided on the inside surface of the skirt 43A, 43B of the caps 40A, 40B, in the vicinity of the free end thereof, only one groove $28'A$, $28'B$ adapted to cooperate with an elastically deformable ring 26A, 26B of this kind, two grooves $27'_{1A}$, $27'_{1B}$—$27'_{2A}$, $27'_{2B}$ are provided, axially staggered heightwise along the transverse axis T, on the outside surface of the corresponding annular bosses 41A, 41B.

As previously, the flanks of the grooves $27'_{1A}$, $27'_{1B}$ are rectilinear and substantially perpendicular to the transverse axis T and the grooves $27'_{1A}$, $27'_{1B}$ are formed at a level corresponding to the engagement of the pegs 20A, 20B with the domes 18A, 18B of the carried pin 14.

On the other hand, the grooves $27'_{2A}$, $27'_{2B}$ are at a level such that the domes 17A, 17B of the pegs 20A, 20B of the carrier pin 13 are considerably set back relative to the corresponding surfaces of the slot 25 in the latter.

As shown in FIG. 9, this provides a snap-fit in the spaced apart standby position of the pegs 20A, 20B adapted to hold the latter securely away from the slot 25 and so to permit insertion of the flange 31 of the carried pin 14 into the slot 25.

As shown, to facilitate the releasable nature of this initial spaced apart standby position, the flank of the groove $27'_{2A}$, $27'_{2B}$ which is nearer the slot 25 is preferably oblique to the transverse axis T.

Also, in the embodiment shown in FIGS. 7 through 10 the flange 31 of the carried pin 14 is solid and thus itself forms the corresponding domes 18A, 18B.

In this embodiment the flange 31 is sheathed over part at least of its circumference by a flexible material tire 45 designed to prevent the extensor tendon of the finger concerned rubbing against a metal part.

In practise this tire 45 forms part of a member 46 which, transversely, forms a flange 47 through a central opening 48 in which the member 46 is engaged over a boss 49 on the flange 31, this boss 49 resulting, for example and as shown here, from simple annularly localized reduction of the thickness of the flange 31.

In the embodiment shown in FIG. 11 a part 50 forming the corresponding dome 17A, 17B is chased into the end of each of the pegs 20A, 20B.

For greater simplicity only one of the pegs 20A, 20B, as it happens the peg 20A, has been shown in FIG. 11.

In the embodiment shown, this is the peg 20A to which is fastened a cap 40A.

However, it is to be understood that the embodiment in question could equally well apply to the embodiment of the peg as shown in FIGS. 1 through 6.

Be this as it may, in the embodiment shown the part 50 is a ball.

It could be an alumina, sapphire or ceramic ball, for example, or even a metal ball.

In the foregoing the domes 17A, 17B of the carrier pin 13 are convex and the corresponding domes 18A, 18B of the carried pin 14 are concave.

As shown in FIG. 12 where, for reasons of simplicity, only one of the domes of the carrier pin 13, as it happens the dome 17A, has been shown, a converse arrangement may be adopted, the domes 17A, 17B of the carrier pin 13 then being concave and the corresponding ones 18A, 18B of the carried pin 14 convex.

In the embodiment shown the domes 18A, 18B of the carried pin 14 may then conjointly form part of a common member 51 chased into the flange 31 of the carried pin 14, for example.

As shown, the member 51 may be a ball, as previously, for example.

In this case the "restriction" means are exclusively provided by the flange 31 of the carried pin 14 cooperating with the arms 21A, 21B of the carrier pin 13 which surround it.

Figure 13:
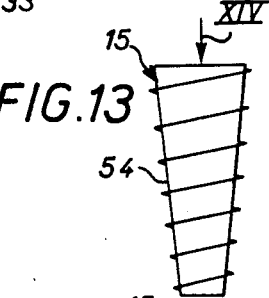
FIG. 13 is a view in elevation of the socket that a joint prosthesis of this kind optionally comprises.
Figure 14:
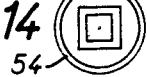
FIG. 14 is a plan view of this socket as seen in the direction of the arrow XI in FIG. 10.

In the embodiment schematically shown in FIGS. 13 and 14 in the case of one of them, as it happens the socket 15, either or both of the sockets 15, 16 preferably associated with the pins 13, 14 of the joint prosthesis 10 in accordance with the invention may be attached by screwing into the bones 11, 12 to be joined, these sockets then having an external screwthread 54 which may be in one piece with them or on a part attached to them.

An advantage of an arrangement of this kind is to enable the position of the sockets 15, 16 in the bones 11, 12 concerned to be corrected by rotation before inserting into the sockets 15, 16 the tails 23, 30 of the corresponding pins 13, 14.

It is to be understood that the present invention is not limited to the embodiments described and shown but encompasses any variant execution and/or combination of the various component parts thereof.

Specifically, although in the foregoing there are preferably associated with the pins of the joint prosthesis in accordance with the invention sockets adapted in particular to confer on the prosthesis the possibility for dislocation, a possibility of dislocation is advantageously retained where such sockets are not used, by virtue of the snap-fit means otherwise employed.

It is sufficient to adapt the snap-fit means appropriately so that they lock the pegs concerned in position in a releasable way.

For example, where these snap-fit means comprise an elastically deformable ring the flanks of the corresponding grooves may be oblique to a greater of lesser degree, as has been described in the case of one of them for the embodiment in which there is provision for such snap-fit means to be operative at two separate levels.

What we claim is:

1. Joint prosthesis comprising two pins each designed to be directly or indirectly inserted into a respective one of the two bones to be joined and, operative between said pins, articulation surfaces comprising, in the case of one of the pins, herein referred to for convenience as the carrier pin, two domes centered on an axis perpendicular to said carrier pin, oriented in opposite directions relative to each other and carried by said carrier pin and, for the other of said pins, herein referred to for convenience as the carried pin, two further domes each complementary to a respective one of the first-mentioned domes and thus adapted to be engaged therewith, carried by said carried pin, this joint prosthesis being generally characterized in that the domes of the carrier pin are carried by respective pegs which are movable transversely relative to the two pins, said carrier pin comprising two arms each having two respective aligned housings in which said pegs are slidably inserted.

2. Joint prosthesis according to claim 1, wherein said housings are open to the outside, so that it is possible to operate on said pegs from the outside.

3. Joint prosthesis according to claim 2, wherein said pegs are fastened to respective caps whereby they cover at least part of the corresponding arms.

4. Joint prosthesis according to claim 3, wherein each of the arms forms an annular boss in which is the corresponding housing and the cap of the associated peg comprises a skirt through which it surrounds said annular boss.

5. Joint prosthesis according to claim 1, wherein there are provided between the pegs and the arms that carry them snap-fit means adapted to lock said pegs in position in their housings.

6. Joint prosthesis according to claim 5, wherein snap-fit means are provided at two different levels.

7. Joint prosthesis according to claim 4, wherein there are provided between the pegs and the arms that carry them snap-fit means adapted to lock said pegs in position in their housings, the snap-fit means being operative between the annular boss on the arms and the skirt of the corresponding cap.

8. Joint prosthesis according to claim 1, wherein the arms of the carrier pin embrace a flange of the carried pin, over the surfaces of which extend the respective domes of the latter.

9. Joint prosthesis according to claim 8, wherein the flange of the carried pin forms a ring into which is chased a member forming the corresponding domes.

10. Joint prosthesis according to claim 8, wherein the flange of the carried pin is solid and itself forms the corresponding domes.

11. Joint prosthesis according to claim 8, wherein the flange of the carried pin has a flexible material tire sheating it over at least part of its periphery.

12. Joint prosthesis according to claim 11, wherein said tire forms part of a member which, transversely, forms a flange through a central opening in which it is engaged on a boss on the flange of the carried pin.

13. Joint prosthesis according to claim 1, wherein each of the pegs is solid and itself forms the dome that it carries.

14. Joint prosthesis according to claim 1, wherein a member forming the corresponding dome is chased onto the end of each peg.

15. Joint prosthesis according to claim 1, wherein there is associated with at least one of the pins a socket into which it is inserted by a tail and relative to which it can move longitudinally.

16. Joint prosthesis according to claim 15, wherein the pin concerned has a pyramid-shaped external contour and the corresponding socket has a pyramid-shaped internal contour complementary to the latter.

17. Joint prosthesis according to claim 6, wherein there are provided between the pegs and the arms that carry them snap-fit means adapted to lock said pegs in position in their housings, the snap-fit means being operative between an annular boss on the arms and a skirt of a corresponding cap.

* * * * *

Disclaimer 4,759,768.—*Thierry Hermann*, Richen, Switzerland; and *Michel Pequignot*, Clamart, France. JOINT PROSTHESIS, IN PARTICULAR FINGER JOINT PROSTHESIS. Patent dated July 26, 1988. Disclaimer filed Dec. 30, 1988, by the inventors.

Hereby enters this disclaimer to the entire term of said patent.
[*Official Gazette May 9, 1989*]

Notice of Adverse Decision in Interference

In Interfernce No. 102,190, involving Patent No. 4,759,768, T. Hermann and M. Pequignot, JOINT PROSTHESIS, IN PARTICULAR FINGER JOINT PROSTHESIS, final judgment adverse to the patentees was rendered June 28, 1989, as to claims 1-5 and 7-15.

*[Official Gazette September 19, 1989.]*